United States Patent [19]
Ball et al.

[11] Patent Number: 6,024,717
[45] Date of Patent: Feb. 15, 2000

[54] APPARATUS AND METHOD FOR SONICALLY ENHANCED DRUG DELIVERY

[75] Inventors: Geoffrey R. Ball, Sunnyvale; Bob H. Katz, Los Gatos, both of Calif.

[73] Assignee: Vibrx, Inc., San Jose, Calif.

[21] Appl. No.: 08/736,302

[22] Filed: Oct. 24, 1996

[51] Int. Cl.$^7$ ................................................. A61B 17/20
[52] U.S. Cl. .............................................. 604/22; 604/49
[58] Field of Search ............................ 604/21, 49, 290; 601/2, 17, 78–81

[56] References Cited

U.S. PATENT DOCUMENTS

| | | | |
|---|---|---|---|
| 1,889,487 | 11/1932 | Nachies . | |
| 2,261,385 | 11/1941 | Kaminsky et al. . | |
| 5,044,356 | 9/1991 | Fishman et al. . | |
| 5,197,946 | 3/1993 | Tachibana | 604/22 |
| 5,267,985 | 12/1993 | Shimada et al. | 604/290 |
| 5,269,291 | 12/1993 | Carter | 128/24 |
| 5,282,785 | 2/1994 | Shapland et al. | 604/21 |
| 5,286,254 | 2/1994 | Shapland et al. | 604/21 |
| 5,315,998 | 5/1994 | Tachibana et al. | 128/660 |
| 5,318,014 | 6/1994 | Carter | 601/2 |
| 5,323,769 | 6/1994 | Bommannan et al. | 601/2 |
| 5,362,309 | 11/1994 | Carter | 604/22 |
| 5,405,614 | 4/1995 | D'Angelo et al. . | |
| 5,445,611 | 8/1995 | Epstein et al. | 604/49 |
| 5,656,016 | 8/1997 | Ogden . | |

OTHER PUBLICATIONS

Mitragotri, Samir et al. "A Mechanistic Study of Ultrasonically–Enhanced Transdermal Drug Delivery," (1995) Journal of Pharmaceutical Sciences, vol. 84, No. 6, pp. 697–706.

Memon, Gopinathan K. et al. "High–Frequency Sonophoresis: Permeation Pathways and Structural Basis for Enhanced Permeability," (1994) Skin Pharmacol, 7:130–139.

Bommannan, D. et al. "Sonophoresis. II. Examination of the Mechanism(s) of Ultrasound–Enhanced Transdermal Drug Delivery," (1992) Pharmaceutical Research, vol. 9, No. 8, pp. 1043–1047.

Bommannan, D. et al. "Sonophoresis. I. The Use of High–Frequency Ultrasound to Enhance Transdermal Drug Delivery," (1992) Pharmaceutical Research, vol. 9, No. 4, pp. 559–564.

Elias, Joel J. "The Microscopic Structure of the Epidermis and Its Derivatives," (1989) Percutaneous Absorption, marcel Dekker, Inc. New Your and Basel, pp. 1–12.

Benson, Heather A. E. "Use of Ultrasound to Enhance Percutaneous Absorption of Benzydamine," (1989) Physical Therapy, vol. 69, No. 2, pp. 113–118.

Pratzel, Helmut et al. "Spontaneous and Forced Cutaneous Absorption of Indomethacin in Pigs and Humans," (1986) The Journal Of Rheumatalogy, vol. 13, No. 6, pp. 1122–1125.

Burnette, Ronald R. "Iontophoresis," Chapter 11, pp. 247–291.

*Primary Examiner*—Mark Bockelman
*Attorney, Agent, or Firm*—Townsend and Townsend and Crew LLP

[57] ABSTRACT

Apparatus for delivering medicament media into tissue comprises a medicament supply assembly and an oscillatory drive assembly. The medicament supply assembly includes a medicament transfer surface, and the oscillatory drive assembly includes a housing, a coil mounted within the housing, and a magnet suspended within the housing. By applying an electrical drive signal to the coil, the housing can be oscillated to phonophoretically enhance delivery of medicament from the medicament transfer surface into tissue.

25 Claims, 7 Drawing Sheets

FIG. 10 ies used in the systems. Thus, it would be desirable to provide phonophoretic drug delivery systems incorporating ultrasonic or other transducers which can use energy more efficiently than piezoelectric transducers. Additionally, piezoelectric transducers require relatively high voltages for excitation. Thus, it would be desirable to provide phonophoretic systems employing ultrasonic transducers which can operate more efficiently and at lower excitation voltages.

APPARATUS AND METHOD FOR SONICALLY ENHANCED DRUG DELIVERY

BACKGROUND OF THE INVENTION

1. Field of the Invention

The present invention relates generally to the field of drug delivery and more particularly to apparatus and methods for the enhanced transdermal and localized internal delivery of drugs to patients.

Drug therapy is the treatment of choice for many diseases and conditions. Drugs may be administered to the patients in a variety of ways, including systemic delivery and localized delivery. Systemic delivery generally requires that the drug enter vascular circulation and may be achieved by conventional techniques, such as injection, oral administration, inhalation, transdermal administration, and the like.

Of particular interest in the present invention, transdermal delivery requires that the drug be systemically absorbed across the patient's skin, usually for an extended period of time. Typically, the drug is incorporated in a matrix or reservoir from which it is released on to the skin. The rate of absorption through the skin can enhanced in several ways, including chemical enhancers, iontophoresis (the application of an external electric field to enhance passage of an ionized drug form across the skin barrier), and phonophoresis (also known as sonophoresis). Of particular interest to the present invention, phonophoresis relies on the application of ultrasonic energy to the drug and/or skin in the region where the drug is being transdermally delivered.

Localized drug delivery can also take a variety of forms. For example, tumors and other localized conditions can be treated by implantation of a drug reservoir or delivery catheter near the diseased site. Intralumenal drug delivery can be effected using catheters having lumens for delivering the drug from an external source to a site of interest. Intralumenal drug delivery has frequently been proposed for the treatment of vascular stenoses and other disease conditions. Enhancement of localized drug delivery from both implants and catheters may be achieved by generally the same methods discussed above in connection with transdermal delivery, i.e. chemical penetration enhancers, iontophoresis, and phonophoresis.

For both transdermal and localized drug delivery, phonophoresis is usually achieved using a piezoelectric ultrasonic transducer which is mechanically or otherwise coupled to the drug or drug delivery device. It is believed that ultrasonic energy enhances the permeability of the outer skin (epidermis) in the case of transdermal delivery, and the tissue or membranes surrounding implants and catheters in the case of localized internal drug delivery. Although the theory of such enhancement is not completely understood, the use of ultrasonic energy for enhancing drug delivery has been quite successful, particularly when employed with proteins, carbohydrates, and other large molecule drugs.

Despite its success, phonophoretic enhancement of drug delivery using piezoelectric ultrasonic transducers suffers from certain drawbacks. For example, piezoelectric ultrasonic transducers generally operate only on a single primary frequency, thus limiting the ability to change the frequency for different applications or change the frequency during the course of a single procedure with a particular patient. Thus, it would be desirable to provide phonophoretic drug delivery systems which allow the frequency to be changed for different uses or during single procedures. Piezoelectric ultrasonic transducers are also relatively inefficient, which can result in excessive power consumption from the batteries used in the systems. Thus, it would be desirable to provide phonophoretic drug delivery systems incorporating ultrasonic or other transducers which can use energy more efficiently than piezoelectric transducers. Additionally, piezoelectric transducers require relatively high voltages for excitation. Thus, it would be desirable to provide phonophoretic systems employing ultrasonic transducers which can operate more efficiently and at lower excitation voltages.

For these reasons, it would be desirable to provide improved phonophoretic drug delivery systems employing transducers meeting at least some of the objectives set forth above. It would be further desirable to provide such systems which can be utilized for both systemic and localized drug delivery, including transdermal delivery, intralumenal delivery, and delivery to internal tissue locations. It would be still further desirable to provide such phonophoretic systems which are low cost, which may be provided as either disposable or reusable (i.e. sterlizable) components. Such apparatus and methods should further be useful as entirely external systems, i.e. with all components located outside the patient's skin, as combined external/internal systems where the power and control component(s) are located externally and the drug delivery component(s) may be transcutaneously implanted or percutaneously delivered to body lumens, or as entirely internal systems where the apparatus may be fully implanted.

2. Description of the Background Art

The use of ultrasonic energy to enhance transdermal drug delivery is described in U.S. Pat. Nos. 5,405,614; 5,323,769; and 5,267,985. The '614 patent notes that sound pulse waves can be produced by transducers which use a coil of wire, but teaches that piezoelectric devices are to be used in transdermal systems. Catheters having ultrasonic enhancement for intralumenal and transcutaneous drug delivery are described in U.S. Pat. Nos. 5,362,309; 5,318,014; 5,315,998; 5,286,254; 5,282,785; 5,269,291; and 5,197,946. Medical publications discussing sonophoresis, phonophoresis, iontophoresis, and related subjects include Pratzel et al. (1986) J. Rheumatol. 13:1122–1125; Burnette, in *Developmental Issues and Research Initiatives*, Hadcraft and Guy, eds., pages 247–288, Marcel Dekker, Inc., New York, (1989); Benson et al. (1989) Phys. Ther. 69:113–118; Bommannan et al. (1992) Pharm. Res. 9:559–564; Elias, in *Percutaneous Absorption*, Bronaugh and Maibach, eds. pages 3–12, Marcel Dekker, Inc., New York (1989); Bommannan et al. (1992) Pharm. Res. 9:1043–1047; Menon et al. (1994) Skin Pharmacol. 7: 130–139; and Mitragotri et al. (1995) J. Pharm. Sci. 84:697–706.

Copending applications assigned to the assignee of the present application which describe the type of floating mass transducer employed in the present device include U.S. application Ser. No. 08/680,578, filed Jul. 12, 1996; U.S. application Ser. No. 08/582,301, filed Jan. 3, 1996; U.S. application Ser. No. 08/568;006, filed Dec. 6, 1995; U.S application Ser. No. 08/526,129; filed Sep. 7, 1995; U.S. application Ser. No. 08/368,219; filed Jan. 3, 1995 now U.S. Pat. No. 5,624,376; U.S. application Ser. No. 08/225,153, filed Apr. 8, 1994, now U.S. Pat. No. 5,554,096; and U.S. application Ser. No. 08/087,618, filed Jul. 1, 1993, now U.S. Pat. No. 5,456,654.

The full disclosures of each of the above-listed U.S. patents and copending applications are hereby incorporated herein by reference.

SUMMARY OF THE INVENTION

Apparatus and methods are provided for delivering a medicament medium to a body surface in a patient. In particular, phonophoretic enhancement of medicament medium delivery is achieved using an oscillatory drive assembly which comprises a housing, a coil attached to the housing, and a magnet suspended within the housing, wherein an electrical drive signal applied to the coil causes oscillation or vibration of the magnet which in turn is transmitted to the housing through the suspension. Such oscillatory drivers are also referred to herein and in the copending applications which have been incorporated herein by reference as "floating mass transducers." The use of such coil-magnet oscillatory drive assemblies is advantageous in a number of respects. First, the drivers may be oscillated at a wide range of frequencies depending primarily on the nature (frequency) of the electrical drive signal which is applied to the coil. This is in contrast to the use of piezoelectric ultrasonic transducers which are limited to a narrow range of inherent vibrational frequencies. Additionally, the coil-magnet oscillatory drivers of the present invention may be programmed to operate efficiently at different frequencies and/or at different periods during the treatment protocol. Piezoelectric transducers have characteristic resonant frequencies and, while they can be driven outside of these frequencies, such operation is significantly less efficient (i.e. requires more energy input). Such variable and/or programmable frequency operation is much more difficult apparatus employing piezoelectric ultrasonic transducers. The oscillatory drive assemblies of the present invention may also be fabricated at relatively low cost, provide for efficient conversion of electrical (battery) energy into mechanical energy, provide for relatively large amplitude when compared to piezoelectric transducers, and further may be operated at low voltages.

Apparatus according to the present invention comprise a medicament supply assembly having a medicament transfer surface and a oscillatory drive assembly. The housing of the oscillatory drive assembly will preferably comprise an interior space and an exterior surface, where the exterior surface is mechanically or fluidly coupled to the medicament transfer surface. That is, the housing will either be connected to or be engaged against the medicament transfer surface in order to directly vibrate such surface, or will be suspended in or engaged against the medicament medium in order to transfer vibrational energy directly into the medium. The coil is attached directly to the housing, usually being fixedly attached but optionally being attached through a resilient or flexible suspension. The magnet is resiliently suspended within the interior housing and is disposed relative to the coil so that the electrical drive signal applied to the coil causes oscillation of the magnet. The oscillation of the magnet, in turn, is transmitted through the suspension to the housing, and the oscillation housing to the medicament transfer surface or medicament medium.

The apparatus of the present invention will usually further comprise an oscillatory driver which is connected to the coil and which produces the electrical drive signal. The oscillatory driver may comprise any conventional oscillatory drive circuitry, and may be adapted to produce a continuous, single frequency or alternatively to be adjustable to produce a range of frequencies and/or pulsed frequencies. Usually, the drive frequency will be ultrasonic, e.g. in the range from 10 kHz to 4 MHz, sonic or usually being in the range from 20 kHz to 400 kHz most often being in the range from 20 kHz to 100 kHz. The oscillatory driver may further be programmable, i.e. it may include digital or analog circuitry which permits the timing (duty cycle) and/or frequency profile of the electrical drive signal to be adjusted over time.

In further preferred aspects of the apparatus of the present invention, the medicament assembly may consist of a single enclosure including a medicament reservoir fluidly coupled to the medicament transfer surface. Typically, the medicament reservoir may comprise a container holding a liquid, gel, or other fluid form of the medicament, which is in direct contact with the medicament transfer surface, which may be a permeable membrane or other conventional release surface. Such single enclosure apparatus will further comprise the oscillatory driver described above together with a battery for powering the driver. Usually, the single enclosure is adapted to be secured to a patient's skin, e.g. by including a pressure adhesive or by taping or strapping to the skin, so that the medicament transfer surface contacts the skin to effect transdermal delivery of the medicament medium. Alternatively, the single enclosure may be adapted to be implanted in patient tissue, in which case the enclosure will usually be coated with a biocompatible material to inhibit immune response.

Apparatus according to the present invention may also comprise a first enclosure and second enclosure. The first enclosure may include the oscillatory drive assembly and a medicament manifold fluidly coupled to distribute medicament to the medicament transfer surface. The second enclosure may include the oscillatory driver, medicament reservoir, and a battery connection to receive a permanent or replaceable battery. Such systems will further comprise a flexible connector extending between the first enclosure and the second enclosure. The flexible connector will include a medicament delivery conduit connecting the medicament reservoir in the first enclosure to the medicament manifold in the second enclosure. The connector will further carry electrical leads from the oscillatory driver in the second enclosure to the oscillatory drive assembly in the first enclosure. Optionally, the second enclosure may further include a pump connected to deliver medicament medium from the reservoir to the medicament delivery conduit. In the absence of the pump, transfer of medicament from the reservoir to the conduit may be effected by capillary forces, absorption, or the like. When a pump is provided, it will usually be connected to the oscillatory driver in order to control the duty cycle of the pump. Optionally, the oscillatory driver may be programmable as described above to turn the pump on and off according to predetermined programs.

Apparatus comprising the first and second enclosure may be utilized externally, or may be partially or wholly implanted. For example, both the first enclosure and the second enclosure may be adapted to be carried externally by the patient. In one instance, the first enclosure may be adapted to be secured to a patient's skin, while the second enclosure may be also be attached to the skin or may be carried on a belt, removable pack, or the like, so that relatively large amounts of drug can be transferred from the second enclosure to the first enclosure. Alternatively, the first enclosure may be adapted to be implanted in patient tissue and the second enclosure adapted to be carried externally, as just described. As a third alternative, both the first enclosure and the second enclosure may be adapted to be implanted in patient tissue.

Although no specific embodiments are illustrated, the apparatus of the present invention may be in the form of an intralumenal catheter where the oscillatory drive assembly is mounted at or near a distal end of the catheter to enhance delivery of medication from the catheter within a body lumen, such as a blood vessel in the patient's vasculature. In such cases, medicament medium will typically be a liquid which is delivered from a proximal end of the catheter external to the patient, through a lumen to a plurality of ports or other release surfaces present at or near the distal end of the catheter.

Methods are also provided for enhancing the delivery of a medicament medium to a body surface. The methods comprise applying the medicament medium to the body surface and phonophoretically enhancing penetration of the medium into tissue underlying the surface. The body surface may be the patient's skin, in which case the delivery methods are referred to as transdermal medicament delivery. Alternatively, the body surface may be internal to the patient, either being within solid tissue or within a body lumen, such as a blood vessel. In all cases, an electrical signal is passed through a coil in a housing, where the coil vibrates a magnet suspended in the housing. Vibration of the magnet in turn causes inertial vibration of the housing, and the vibrational energy is transmitted from the housing to the medicament medium and/or the body surface to phonophoretically enhance penetration of the medicament through the tissue surface. The medicament medium may be in any conventional form, such as a liquid medicament, a gel medicament, a suspension, microporous particles, or the like. Such methods are preferably carried out using the apparatus described above. Usually, the electrical signal applied to the coil has a voltage in the range from 1V to 20V. The amplitude of vibration (displacement) is typically in the range from 1 μm to 100 μm.

DESCRIPTION OF THE SPECIFIC EMBODIMENTS

Apparatus and methods according to the present invention are useful for delivering a wide variety of medicament medium to a patient. As described in greater detail herein below, the medicament medium may be delivered transdermally, transcutaneously, intralumenally, and within solid tissue sites, where in all cases absorption of the medicament or a pharmacologically active portion thereof into the underlying or surrounding tissue is phonophoretically enhanced by the application of ultrasonic or sonic energy. The medicament medium may take any conventional form, including liquids, gels, porous reservoirs, inserts, or the like, and the medicament or pharmacologically active portion thereof may be intended to treat or alleviate an existing condition or prophylactically prevent or inhibit another condition of the patient. The effect of the medicament may be local, such as providing for anti-tumor treatment, or may be systemic. Suitable medicaments include broad classes of compounds normally delivered through the skin and other body surfaces or into solid tissues. In general, such medicaments include or incorporate anti-invectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimatics; xanthine derivatives; cardiovascular preparations including potassium and calcium channel blockers, beta-blockers, and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs may be delivered as can drugs of either high or low molecular weight.

Proteinaceous and polypeptide drugs represent a preferred class of drugs for use in conjunction with the presently disclosed and claimed invention. Such drugs cannot generally be administered orally in that they are often destroyed in the gastrointestinal tract or metabolized in the liver. Further, due to the high molecular weight of most polypeptide drugs, conventional transdermal delivery systems are not generally effective. It is also desirable to use the method of the invention in conjunction with drugs to which the permeability of the skin is relatively low, or which give rise to a long lag-time. (Application of ultrasound as described herein has been found to significantly reduce the lag-time involved with the transdermal administration of most drugs).

The floating mass transducer includes a magnet disposed inside a housing. The magnet generates a magnetic field and is capable of movement within the housing. A coil is also disposed within the housing but, unlike the magnet, the coil is not free to move within the housing. When an alternating current (an electrical drive signal described below) is provided to the coil, the coil generates a magnetic field that interacts with the magnetic field of the magnet, causing the magnet and coil/housing to vibrate relative to each other. The vibration of the housing is transferred to the medicament and/or medicament transfer surface to enhance absorption of the medicament into underlying tissue. Alternatively, the coil or coils may be secured to an outside surface of the housing.

The housing will usually be sealed, particularly for implantable devices where openings might increase the risk of infection. The housing will be proportioned to fit within an enclosure for the phonophoretic stimulation of medicament released from said enclosure. While the present invention is not limited by the shape of the housing, it is preferred that the housing is of a cylindrical capsule shape. Similarly, it is not intended that the invention be limited by the composition of the housing. In general, it is preferred that housings intended for implantation be composed of, and/or coated with, a biocompatible material.

The housing contains or supports both the coil and the magnet assembly. Typically, the magnet assembly is positioned in such a manner that it can oscillate freely without colliding with either the coil or the interior of the housing itself. When properly positioned, a permanent magnet within the assembly produces a predominantly uniform flux field. Although permanent magnets are preferred (to conserve energy), electromagnets could also be used.

When the alternating current is delivered to the housing, attractive and repulsive forces are generated by the interaction between the magnet and the coil. Because the coil is more rigidly attached to the housing than the magnet assembly, the coil and housing move together as a unit as a result of the forces produced. The vibrating transducer triggers sound perception of the highest quality when the relationship between the housing's displacement and the coil's current is substantially linear. Such linearity is best achieved by positioning and maintaining the coil within the substantially uniform flux field produced by the magnet assembly.

Figure 1:
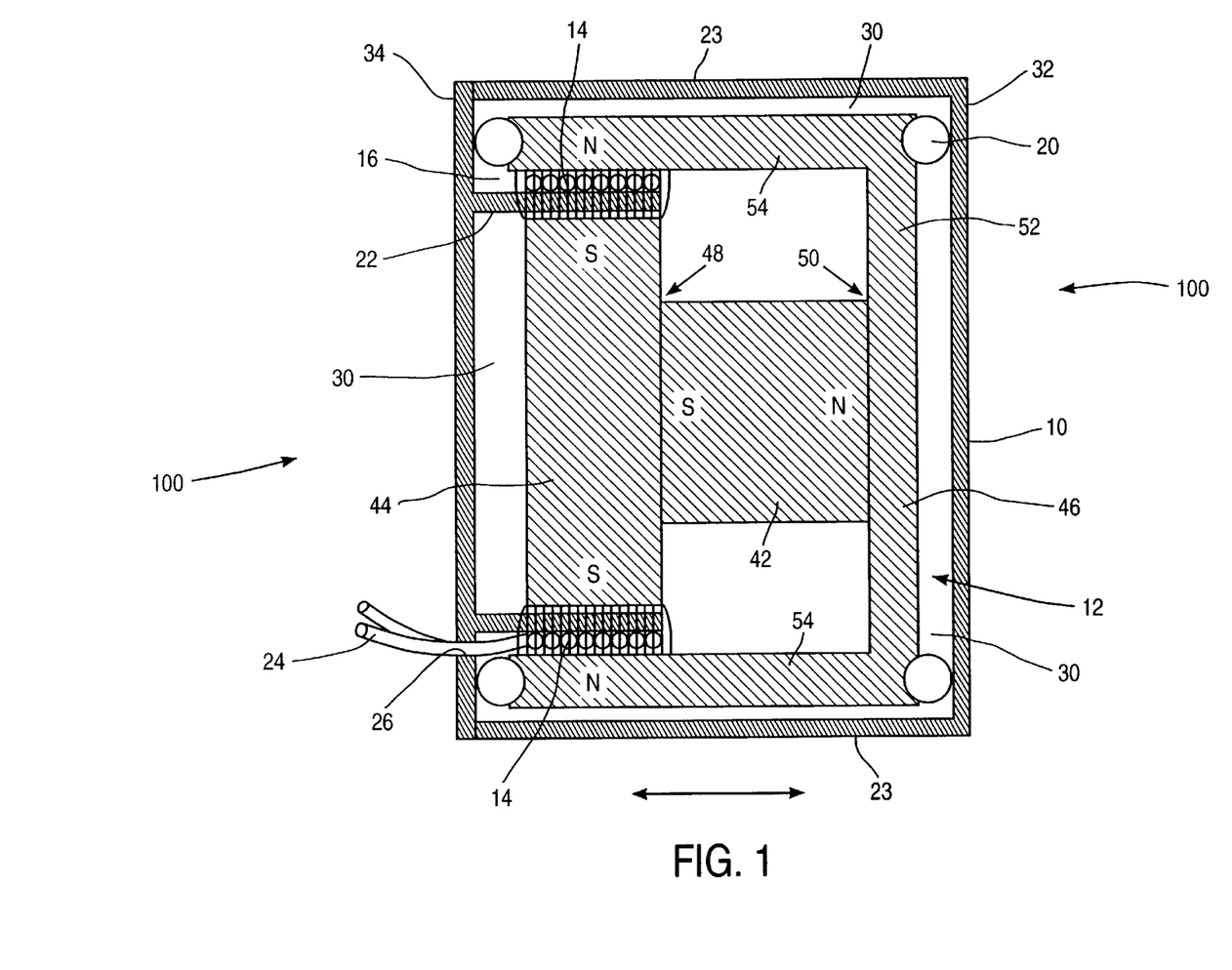
FIGS. 1 and 2 illustrate a first embodiment of a floating mass transducer suitable for use in the oscillatory drive assembly of the apparatus of the present invention.
Figure 2:
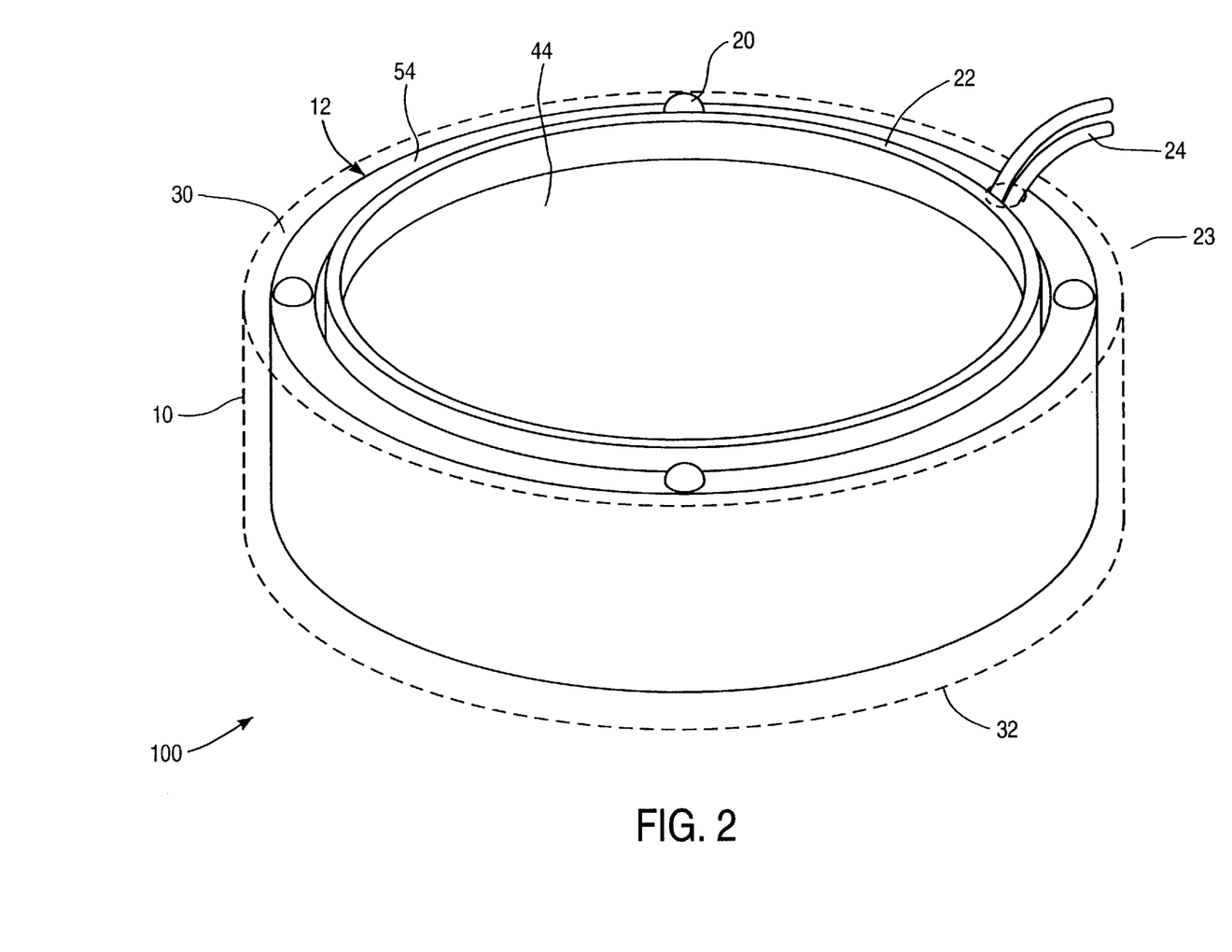

A preferred embodiment of a floating mass transducer according to the present invention is shown in FIGS. 1 and 2. In this embodiment, the floating mass is a magnet. The transducer 100 is generally comprised of a sealed housing 10 having a magnet assembly 12 and a coil 14 disposed inside it. The magnet assembly is loosely suspended within the housing, and the coil is rigidly secured to the housing. As will be described, the magnet assembly 12 preferably includes a permanent magnet 42 and associated pole pieces 44 and 46. When alternating current is conducted to the coil, the coil and magnet assembly oscillate relative to each other and cause the housing to vibrate. The housing 10 is proportioned to be attached within. An exemplary housing is preferably a cylindrical capsule having a diameter in the range from 0.5 mm to 4 mm and a thickness in the range from 2 mm to 4 mm, and is made from a biocompatible material such as titanium. Preferably, is at the lower side of the diameter range in order to fit in small catheters (on the order of 1 mm (3 French) in diameter) to access the coronary vasculature. The housing has first and second faces 32, 34 that are substantially parallel to one another and an outer wall 23 which is substantially perpendicular to the faces 32, 34. Affixed to the interior of the housing is an interior wall 22 which defines a circular region and which runs substantially parallel to the outer wall 23.

The magnet assembly 12 and coil 14 are preferably sealed inside the housing. Air spaces 30 surround the magnet assembly so as to separate it from the interior of the housing and to allow it to oscillate freely without colliding with the coil or housing. The magnet assembly is connected to the interior of the housing by flexible membranes such as silicone buttons 20. The magnet assembly may alternatively be floated on a gelatinous medium such as silicone gel which fills the air spaces in the housing. A substantially uniform flux field is produced by configuring the magnet assembly as shown in FIG. 1. The assembly includes a permanent magnet 42 positioned with ends 48, 50 containing the south and north poles substantially parallel to the circular faces 34, 32 of the housing. A first cylindrical pole piece 44 is connected to the end 48 containing the south pole of the magnet and a second pole piece 46 is connected to the end 50 containing the north pole. The first pole piece 44 is oriented with its circular faces substantially parallel to the circular faces 32, 34 of the housing 10. The second pole piece 46 has a circular face which has a rectangular cross-section and which is substantially parallel to the circular faces 32, 34 of the housing. The second pole piece 46 additionally has a pair of walls 54 which are parallel to the wall 23 of the housing and which surrounds the first pole piece 44 and the permanent magnet 42.

The pole pieces should be manufactured out of a magnetic material such as ferrite or SmCo. They provide a path for the magnetic flux of the permanent magnet 42 which is less resistive than the air surrounding the permanent magnet 42. The pole pieces conduct much of the magnetic flux and thus cause it to pass from the second pole piece 46 to the first-pole piece 44 at the gap in which the coil 14 is positioned.

For the device to operate properly, it should vibrate the medicament and/or medicament transfer surface with sufficient force and at frequency(ies) such that the absorption of the medicament medium into tissue is enhanced. The force of vibrations are best maximized by optimizing two parameters: the mass of the magnet assembly relative to the combined mass of the coil and housing, and the energy product (EP) of the permanent magnet 42.

The ratio of the mass of the magnet assembly to the combined mass of the magnet assembly, coil and housing is most easily optimized by constructing the housing of a thinly machined, lightweight material such as titanium and by configuring the magnet assembly to fill a large portion of the space inside the housing, although there must be adequate spacing between the magnet assembly and the housing and coil for the magnet assembly to vibrate freely within the housing.

The magnet should preferably have a high energy product. NdFeB magnets having energy products of forty-five and SmCo magnets having energy products of thirty-two are presently available. A high energy product maximizes the attraction and repulsion between the magnetic fields of the coil and magnet assembly and thereby maximizes the force of the oscillations of the transducer. Although it is preferable to use permanent magnets, electromagnets may also be used in carrying out the present invention.

When the magnet assembly, coil, and housing are configured as in FIG. 1, alternating current in the coil causes the housing to oscillate side-to-side in the directions indicated by the double headed arrow in FIG. 1. FIG. 2 is a partial perspective view of the transducer of FIG. 1. The transducer is most efficient when positioned such that the side-to-side movement of the housing produces side-to-side movement of the medicant and/or medicant transfer surface.

Figure 3:
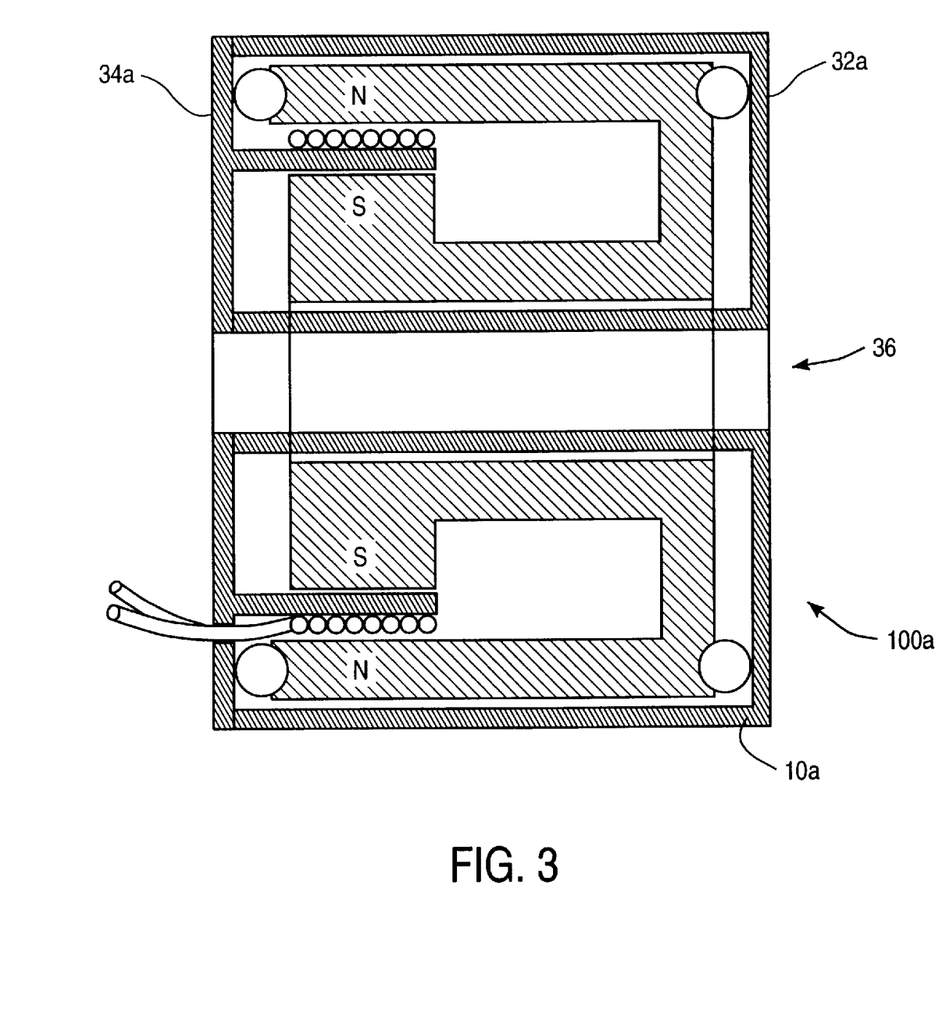
FIG. 3 illustrates an alternative floating mass transducer suitable for use in the apparatus of the present invention similar to that of FIG. 1, and including a lumen through its center to permit the passage and delivery of medicament medium.

An alternate transducer 100a having an opening 36 through the center is illustrated in FIG. 3. The opening 36 passing from the first face 32a to the second face 34a of the housing and is thereby annularly shaped. The opening 36 is useful for mounting the transducer within a housing and/or for delivering drug therethrough. For example, the transducer 100a could be mounted in the distal end of the intravascular or other intralumenal catheter with the opening 36 forming a portion of a medicament delivering lumen through the catheter.

Figure 4:
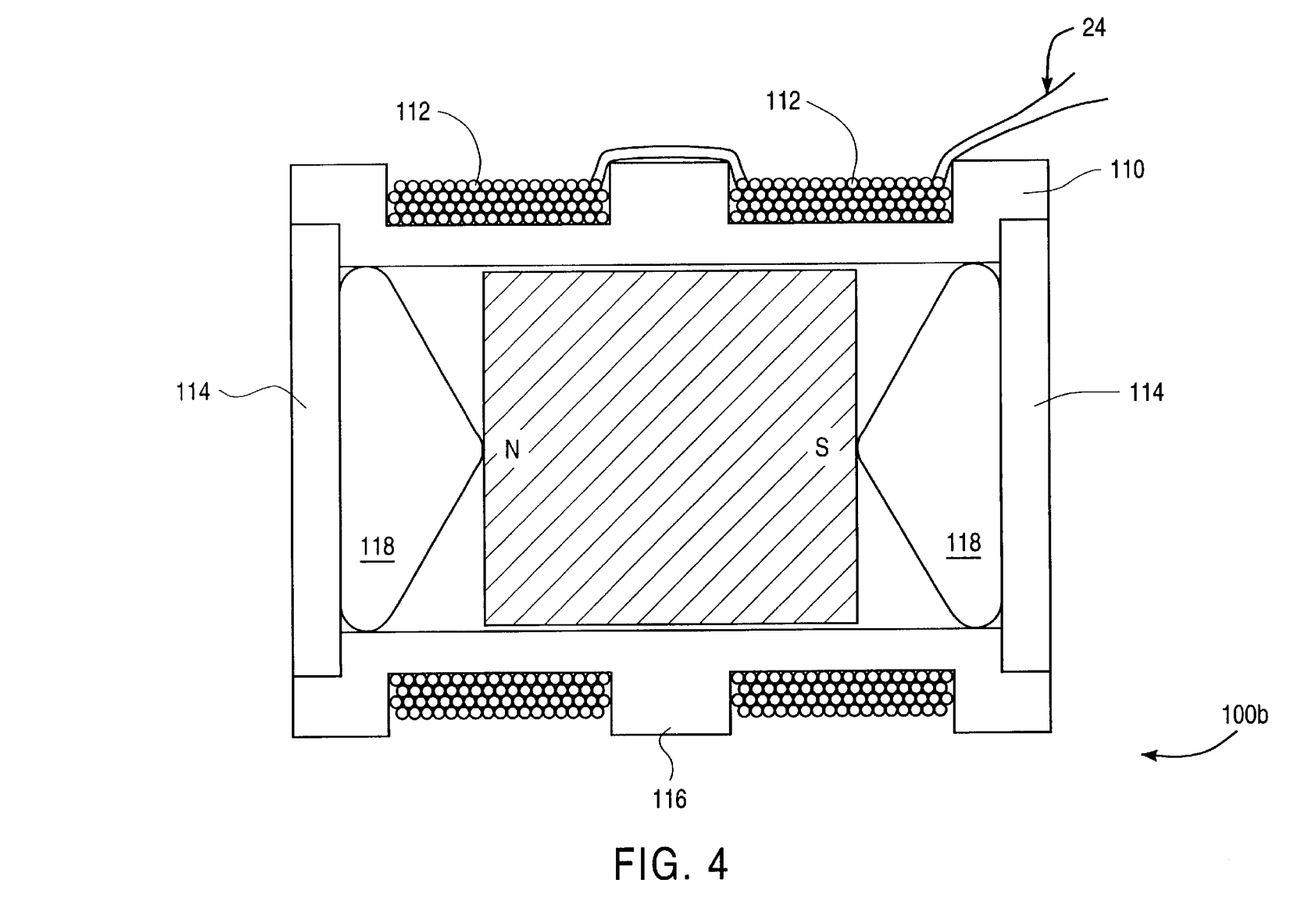
FIG. 4 illustrates a second alternative floating mass transducer employing an external coil on the transducer housing.

In FIG. 4, floating mass transducer 100b has a cylindrical housing 110. The housing 110 has a pair of notches on the outside surface to retain or secure a pair of coils 112. The coils may be made of various metallic materials including gold and platinum. The housing 110 retains the coils much like a bobbin retains thread. The housing includes a pair of end plates 114 that seal the housing. The housing may be constructed of materials such as titanium, stainless steel, aluminum, nylon, and platinum. In one embodiment, the housing 110 is constructed of titanium and the end plates are laser welded to hermetically seal the housing.

Within the housing is a cylindrical magnet 116 which may be a SmCo magnet. The magnet is not rigidly secured to the inside of the housing. Instead, a biasing mechanism supports, and may actually suspend, the magnet within the housing. As shown, the biasing mechanism is a pair of soft silicone cushions 118 that are on each end of the magnet. Thus, the magnet is generally free to move between the end plates subject to the retention provided by the silicone cushions within the housing. Although silicone cushions are shown, other biasing mechanisms like springs and magnets may be utilized.

When an electrical drive signal passes through coils 112, the magnetic field generated by the coils interacts with the magnetic field of magnet 116. The interaction of the magnetic fields causes the magnet to vibrate within the housing. Preferably, the windings of the two coils are wound in opposite directions to get a good resultant force on the magnet (i.e., the axial forces from each coil do not cancel each other out). The magnet vibrates within the housing and is biased by the biasing mechanism within the housing. The resonant frequency of the floating mass transducer may be determined by the "firmness" by which the biasing mechanism biases the magnet. For example, if a higher resonant frequency of the floating mass transducer is desired, springs with a relatively high spring force may be utilized as the biasing mechanism. Alternatively, if a lower resonant frequency of the floating mass transducer is desired, springs with a relatively low spring force may be utilized as the biasing mechanism.

It is known that an electromagnetic field in the vicinity of a metal induces a current in the metal. Such a current may oppose or interfere with magnetic fields. Although a thin metal layer such as titanium separates coils 112 and magnet 116, if the metal layer is sufficiently thin (e.g., 0.05 mm) then the electromagnetic interference is negligible. Additionally, the housing may be composed of a nonconducting material such as nylon. In order to reduce friction within the housing, the internal surface of the housing and/or the magnet may also be coated to reduce the coefficient of friction.

Apparatus according to the present invention will further include an oscillatory driver including the drive circuitry necessary to produce an alternating current signal which is delivered to the coil to vibrate the magnet. The oscillatory driver may be included in the same enclosure as the oscillatory drive assembly, including the medicament supply assembly and other components described below. Alternatively, the oscillatory driver may be mounted in a separate enclosure from that which holds the oscillatory drive assembly. The use of single enclosure apparatus including all components necessary to phonophoretically enhance medicament delivery is preferred for transdermal delivery, where the enclosure may be attached to the patient's skin as a patch or other conventional unit. Separation of the oscillatory driver from the oscillatory drive assembly, in contrast, is preferred when the oscillatory drive assembly is to be implanted or when relatively large volumes of medicament are to be carried in the medicament supply assembly.

The driver may comprise a simple oscillatory circuit which produces a single, continuous frequency, typically in the range from 10 kHz to 4 MHz, usually in the range from 20 kHz to 400 kHz, more usually in the range from 20 kHz to 100 kHz. Alternatively, the oscillatory circuitry may be connected to separate digital or analog circuitry for programming operation of the oscillator. For example, the oscillator may be programmed to vary its duty cycle (i.e., on-off operation over time), frequency, amplitude (power), or the like. The ability to prepare oscillatory circuitry and compatible programmable circuitry is well within the skill in the art and need not be described further herein.

The oscillatory driver will be connected to a battery to provide power to the oscillatory drive assembly. Preferably, a high energy density battery, such as a lithium, nickel-cadmium, or other battery will be employed. The battery may be incorporated as a permanent part of the oscillatory drive assembly, or may be removable and replaceable.

Figure 5:
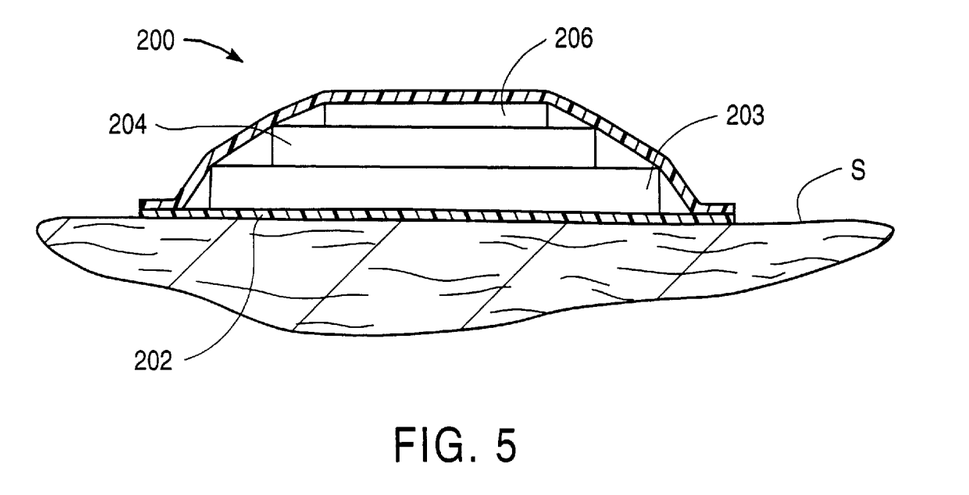
FIG. 5 illustrates a single enclosure embodiment of the medicament medium delivery apparatus of the present invention.
Figure 6:
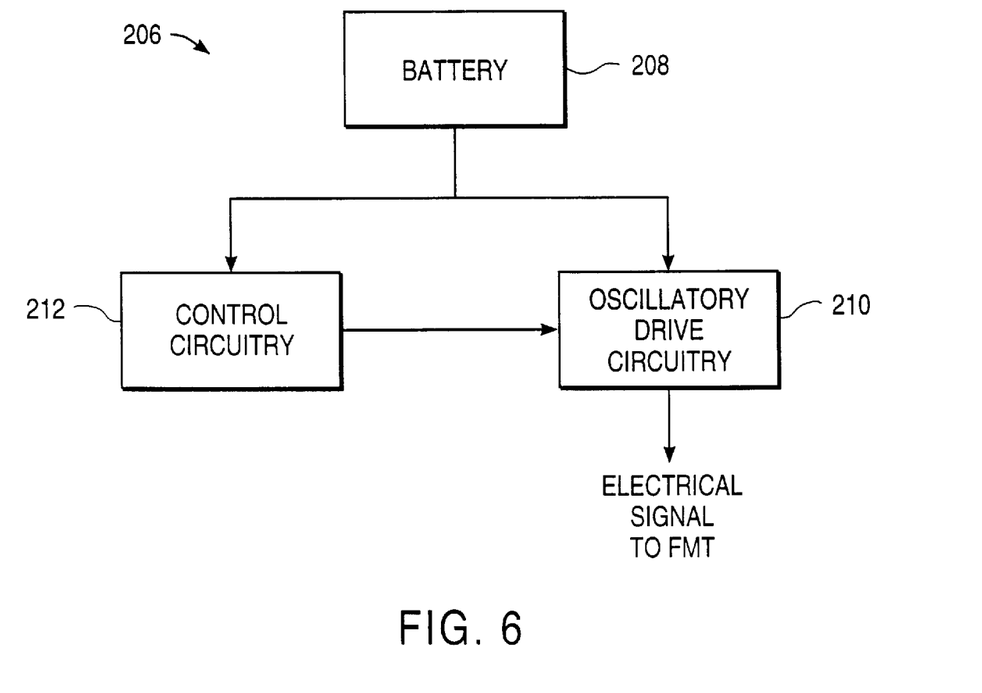
FIG. 6 is a block diagram illustrating the oscillatory driver of the medicament delivery apparatus of FIG. 5.

Referring now to FIGS. 5 and 6, a first embodiment of the apparatus of the present invention intended for transdermal drug delivery will be described. An enclosure 200 in the form of a transdermal patch comprises a medicament reservoir 202, an oscillatory drive assembly 204, and an oscillatory driver 206. The oscillatory drive assembly may comprise any of the floating mass transducers described above in connection with FIGS. 1–4. The oscillatory driver is shown schematically in FIG. 6 and comprises a battery 208 (which will usually be permanently affixed within the driver 206), oscillatory drive circuitry 210, and control circuitry 212. The battery will power both the control circuitry 212 and the oscillatory drive circuitry 210. The control circuitry 212 will typically comprise digital circuitry which is pre-programmed to control the frequency, duty cycle, and/or power amplitude of the output of the oscillatory drive circuitry 210. The output electrical signal from the drive circuitry 210 is connected to the floating mass transducer (FMT) through connecting wires (not shown) extending from the oscillatory driver 206 to the oscillatory drive assembly 204.

The enclosure 200 comprises a permeable membrane 202 which permits the flow of medicament from the medicament reservoir 220 onto the surface of the patient's skin S. The membrane 202 may optionally be a rate-controlling membrane. Alternatively, the absorption rate may be controlled primarily by the oscillations of the oscillatory drive assembly 204. In the embodiment of FIG. 5, vibrational energy from the oscillatory drive assembly 204 is transmitted directly into the medicament then medicament reservoir 220. Such energy is ultimately transferred through the membrane 202 and into the skin in order to enhance penetration of the medicament through the skin.

Figure 7:
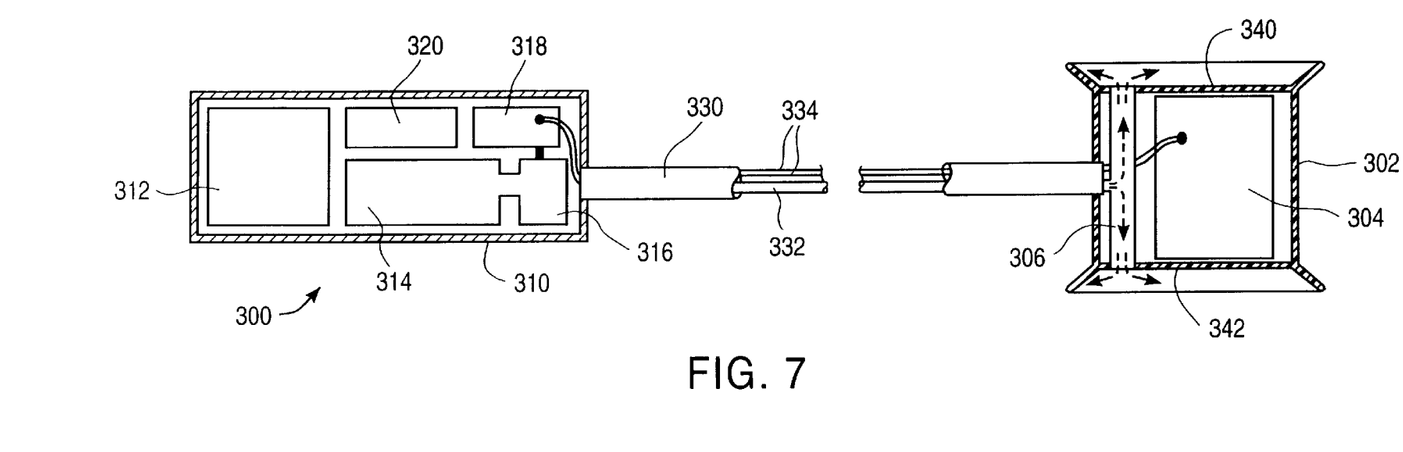
FIG. 7 illustrates a two enclosure embodiment of the medicament medium delivery apparatus of the present invention.
Figure 8:
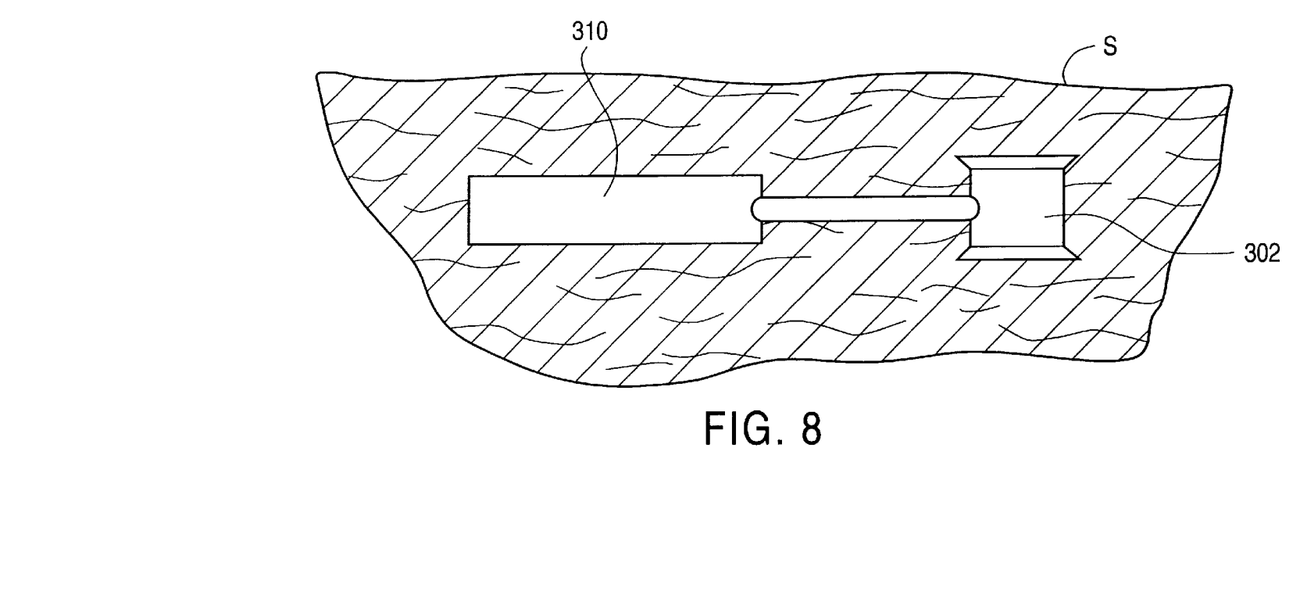
FIG. 8 illustrates the medicament delivery apparatus of FIG. 7 fully implanted in solid tissue.
Figure 9:
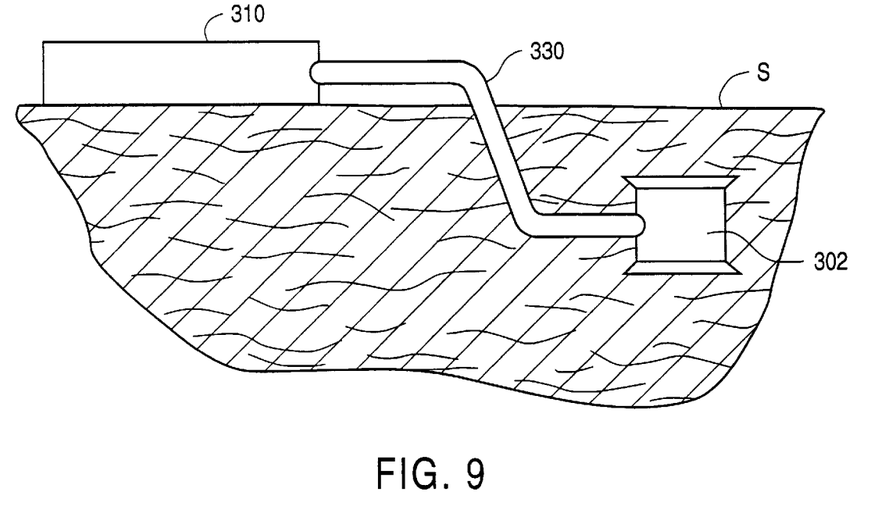
FIG. 9 illustrates the medicament delivery apparatus of FIG. 7, wherein a first medicament delivery enclosure is implanted and a second control enclosure is mounted on the patient's skin.
Figure 10:
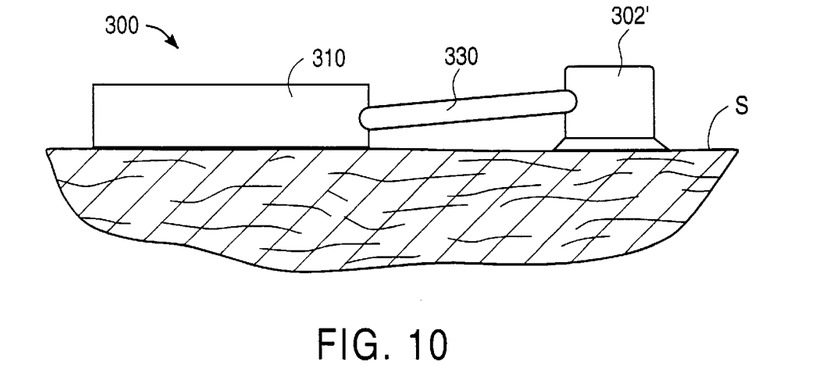
FIG. 10 illustrates the medicament delivery apparatus of FIG. 7, where both the first and second enclosures are mounted on the patient's skin.

Referring now to FIG. 7, an alternative embodiment of apparatus according to the present invention is illustrated. Apparatus 300 comprises a first enclosure 302 which includes an oscillatory drive assembly 304 (which may be in the form of any of the floating mass transducers described in FIGS. 1–4 above) and a medicament distribution manifold 306 therein. A second enclosure 310 includes a battery 312 (and which is optionally removably held within the enclosure 310), the medicament reservoir 314, a pump 316, an oscillatory driver 318, and control circuitry 320. The first enclosure is attached to the second enclosure by a flexible connector 330 which is typically in the form a sealed or fully enclosed tube. The tube will usually be formed from a plastic. In the implantable embodiments discussed below, all materials must be biocompatible and will usually be coated with a material which inhibits immune response. A medicament conduit 332 runs through the connector 330 from the pump 316 to the distribution manifold 306. Additionally, wires 334 run through the connector 330 from the oscillatory driver 318 to the oscillatory drive assembly 304. The oscillatory driver 318 may be controlled by the circuitry 320 to vary the duty cycle, frequency of operation, amplitude and other perimeters, as generally discussed above. In addition, the oscillatory driver 318 will usually control operation of the pump 316 which directs medicament from the reservoir 314 to the distribution manifold 306. The medicament is distributed over a first distribution surface 340 and a second distribution surface 342 on the first enclosure 302. The distribution surface 340 and 342 will each form a small region when implanted within solid tissue, as shown in FIGS. 8 and 9 below. Alternatively, the enclosure 302 may include only a single distribution surface for transdermal delivery, as shown in FIG. 10 below. Release of medicament from the distribution manifold 306 to the distribution surfaces 340 and 342 are shown by broken-line arrows in FIG. 7.

The apparatus 300 of FIG. 7 may be fully implanted within solid tissue, as shown in FIG. 8. Alternatively, the apparatus 300 of FIG. 7 may be mounted transcutaneously, as shown in FIG. 9, where the first enclosure 302 is implanted within tissue beneath the patient's skin S and the second enclosure 310 is secured externally to the patient, optionally attached to the skin. Alternatively, the enclosure 310 could be mounted in a belt, pack, or other convenient means for carrying by the patient. In a third alternative, the apparatus 300 may be mounted entirely externally to the patient, with the first enclosure 302 prime (modified to include a single distribution surface) secured to the patient's skin and the second enclosure 310 mounted elsewhere on the patient's skin.

Although the foregoing invention has been described in detail for purposes of clarity of understanding, it will be obvious that certain modifications may be practiced within the scope of the appended claims.

What is claimed is:

1. Apparatus for delivering a medicament medium to a patient, said apparatus comprising:
    a medicament supply assembly having a medicament transfer surface; and
    an oscillatory drive assembly in the medicament supply assembly including:
        (a) a housing having an interior space and an exterior surface, wherein the exterior surface is mechanically or fluidly coupled to the medicament transfer surface;
        (b) a coil attached to the housing and disposed in the interior space; and
        (c) a magnet suspended within the interior of the housing, wherein an electrical drive signal applied to the coil causes oscillation of the magnet relative to the housing which produces an inertial force which is transmitted to the medicament transfer surface by the housing.

2. Apparatus as in claim 1, further comprising an oscillation driver which is connected to the coil and which produces the electrical drive signal.

3. Apparatus as in claim 2, wherein the oscillatory driver is programmable.

4. Apparatus as in claim 2, wherein the medicament supply assembly consists of a single enclosure including a medicament reservoir fluidly coupled to the medicament transfer surface, a battery connected to the oscillatory driver, and the oscillatory driver therein.

5. Apparatus as in claim 4 wherein the single enclosure is adapted to be secured to a patient's skin so that the medicament transfer surface contacts the skin to effect transdermal delivery of the medicament medium.

6. Apparatus as in claim 4, wherein the single enclosure is adapted to be implanted in patient tissue.

7. Apparatus as in claim 6, wherein the single enclosure is coated with a biocompatible material to inhibit immune response.

8. Apparatus as in claim 2, wherein the medicament supply assembly comprises:
    a first enclosure including the oscillatory drive assembly and a medicament manifold fluidly coupled to distribute medicament to the medicament transfer surface;
    a second enclosure including the oscillatory driver, a medicament reservoir, and a battery connection; and
    a flexible connector extending between the first enclosure and the second enclosure and including a medicament delivery conduit connecting the reservoir to the manifold and electrical leads connecting the oscillatory driver to the oscillatory drive assembly.

9. Apparatus as in claim 8, wherein the second enclosure further includes a pump connected to deliver medicament from the reservoir to the medicament delivery conduit.

10. Apparatus as in claim 9, wherein the oscillatory driver connected to the pump and programmable to selectively actuate the pump to deliver medicament to the medicament transfer surface.

11. Apparatus as in claim 8, wherein first enclosure is adapted to be secured to a patient's skin and the second enclosure adapted to be carried externally by the patient.

12. Apparatus as in claim 8, wherein the first enclosure is adapted to be implanted in patient tissue and the second enclosure is adapted to be carried externally by the patient.

13. Apparatus as in claim 8, wherein the first and second enclosures are adapted to be implanted in patient tissue.

14. A method for enhancing the delivery of a medicament medium to a body surface, said method comprising:
    applying the medicament medium to the body surface;
    passing an electrical signal through a coil attached to a housing, wherein the coil vibrates a suspended magnet relative to the housing and the magnet causes inertial vibration of the housing; and
    transmitting vibrational energy from the housing to the medicament medium and/or the body surface to enhance penetration of the medicament medium into the tissue surface.

15. A method as in claim 14, wherein the medicament medium comprising a liquid, a gel, a suspension, or microporous particles.

16. A method as in claim 14, wherein the body surface is skin and the medicament is applied by engaging a medicament transfer surface against the skin.

17. A method as in claim 16, wherein the vibrational energy is transmitted to the medicament transfer surface.

18. A method as in claim 14 wherein the body surface is internal tissue and the medicament is applied by implanting a medicament transfer surface in the tissue.

19. A method as in claim 18, further comprising the step of implanting an enclosure which includes the medicament transfer surface and the housing.

20. A method as in claim 19, wherein the electrical signal is generated within the enclosure and medicament is supplied to the medicament transfer surface from a reservoir disposed within the enclosure.

21. A method as in claim 19, wherein the electrical signal is generated externally of the patient and delivered transcutaneously to the coil in the enclosure.

22. A method as in claim 21, wherein the medicament is supplied to the medicament transfer surface from a reservoir disposed within the enclosure.

23. A method as in claim 21, wherein the medicament is delivered to the medicament transfer surface from a reservoir disposed externally of the patient.

24. A method as in claim 14, wherein the electrical signal vibrates the magnet at a frequency in the range from 10 kHz to 4 MHz.

25. A method as in claim 14, wherein the electrical signal has a voltage in the range from 1V to 20V.

* * * * *